United States Patent
Mauleon et al.

(10) Patent No.: US 6,673,977 B2
(45) Date of Patent: Jan. 6, 2004

(54) PROCEDURE AND DEVICE FOR THE ALKYLATION OF ISOBUTANE BY LIGHT OLEFINS

(75) Inventors: Jean-Louis Mauleon, Sainte Croix sur Aizier (FR); Pedro Nascimento, Le Havre (FR)

(73) Assignee: Total Raffinage Distribution S.A., Puteaux (FR)

( * ) Notice: Subject to any disclaimer, the term of this patent is extended or adjusted under 35 U.S.C. 154(b) by 0 days.

(21) Appl. No.: 09/739,655

(22) Filed: Dec. 20, 2000

(65) Prior Publication Data

US 2001/0034468 A1 Oct. 25, 2001

(30) Foreign Application Priority Data

Dec. 23, 1999 (FR) .............................................. 99 16375

(51) Int. Cl.[7] .............................. C07C 2/56; C07C 2/58
(52) U.S. Cl. ...................... 585/331; 585/332; 585/719; 585/737; 585/747; 585/748; 585/743
(58) Field of Search ................................. 585/714, 720, 585/737, 747, 748, 743, 331

(56) References Cited

U.S. PATENT DOCUMENTS 2,394,906 A   2/1946  Frey .......................... 585/313
3,931,352 A * 1/1976  Mikulicz ..................... 585/332
4,324,937 A   4/1982  Vora ........................... 585/315
5,629,257 A * 5/1997  Umansky et al. ........... 502/217

FOREIGN PATENT DOCUMENTS

| WO | WO 97/19752 | * | 6/1997 |
| WO | WO 98/25699 | * | 6/1998 |

* cited by examiner

Primary Examiner—Thuan D. Dang
(74) Attorney, Agent, or Firm—Sughrue Mion, PLLC

(57) ABSTRACT

A procedure for the alkylation of isobutane by olefinic hydrocarbons, in which a first hydrocarbon charge (3) rich in isobutane is put in contact with a second hydrocarbon charge rich in light olefins (2), under conditions that will provoke the alkylation of the isobutane by the light olefins, the effluents that emanate from the reaction area in a fractionation column (6) are treated in order to extract therefrom at least a first cut rich in alkylate (7), a second cut rich in normal butane (8) and a third cut rich in isobutane (9), said third cut (9) is then recycled at the entry of the alkylation reaction area. The second cut (8) rich in normal butane is purified (12) so as to lower its content in compounds with 5 or more carbon atoms to a value that is less than or equal to 5% by weight, the cut thus purified (14) is treated in an isomerization reactor (16) of normal butane to isobutane, this cut is then recycled (21) at the entry of the alkylation effluents fractionation column (6).

13 Claims, 2 Drawing Sheets

PROCEDURE AND DEVICE FOR THE ALKYLATION OF ISOBUTANE BY LIGHT OLEFINS

BACKGROUND OF THE INVENTION

This invention is an improvement to procedures for the alkylation of isobutane by light olefins. More specifically, this invention relates to a procedure for the alkylation of isobutane by olefinic hydrocarbons in which a cut rich in normal butane is extracted from the reaction effluents, where said cut is upgraded by isomerization so as to produce isobutane intended for recycling in the alkylation unit.

The invention also relates to a device for implementing such a procedure.

As of 1930 the refiners developed alkylation procedures in which branched paraffins (or isoparaffins) react with olefins to create branched superior hydrocarbons, essentially intended to be incorporated in aviation gasoline, or to formulate high octane rating automobile gasoline.

The industrial conditions for implementation of the isobutane alkylation reaction by light olefins are well known to those skilled in the art. Indeed we can refer to the article by J. F. Joly, in the work entitled Procédés de Transformation (Le Raffinage du Pétrole, Vol. 3, Chap. 7; Edition Technip 1998). In general, two charges, one containing isobutane and the other containing light olefins, are put in contact in an alkylation reactor, in the presence of a liquid or solid acid type catalyst. The reaction effluents are then treated in a fractionation area, in which the product sought, the alkylate, is separated through distillation in the form of a hydrocarbon mixture that contains for the most part 5 to 12 carbon atoms.

In a manner known in itself, the relative quantities of isobutane and olefins introduced in the alkylation unit make up a key parameter in the procedure's implementation. Indeed, the isobutane/olefin ratio not only conditions the reaction's yield, but also the quality of the alkylate that is produced. We know it is essential to use a large excess of isobutane compared with the olefins, in order to limit the secondary polymerization reactions of the olefins. This is why it is normal, in the industrial alkylation units, to operate with an isobutane-to-olefins molar ratio ranging between 3 and 25 based on the type of unit.

It is therefore necessary to have a large source of isobutane to feed the alkylation unit. Yet, isobutane is usually produced in limited quantities in refineries, unless, upstream from the alkylation, a unit such at those described in the article by G. L. Frischkorn, P. J. Kuchar and R. K. Olson, Energy Progress, 8(3), 154, 1988 that are specifically intended for the production of isobutane through isomerization of the normal butane is built, however this represents a costly investment.

Therefore, the quantity of available isobutane often limits the capacities of the alkylation industrial units. Consequently, we understand why it is customary to recuperate the excess isobutane that did not react in a reaction effluent fractionation column and to recycle it in the alkylation reactor.

It is also customary to separate the normal butane that is usually present in these effluents in the reaction effluent fractionation column. Indeed, the cut rich in normal butane thus obtained is directly amenable to beneficiation: it is usually incorporated in products such as gasoline or liquid petroleum gas (LPG).

A particularly advantageous practice consists in subjecting this cut rich in n-butane to an isomerization treatment which makes it possible to transform the normal butane into isobutane that can then be recycled in the alkylation unit. This solution, mentioned for example in the U.S. Pat. No. 5,675,052 is that much more interesting for the refiner as it makes it possible to better beneficiate the normal butane that is extracted from the effluents in order to produce an isobutane make-up intended to feed the procedure.

This solution also appears in the U.S. Pat. No. 5,565,617 that describes a fractionation system and a specific treatment adapted to the effluents emitted from an alkylation reactor in which the reaction is done in the presence of a solid acid catalyst and a halogen compound. This treatment, intended to eliminate halides that are present in the effluents, also incorporates, as an option, a step for drawing off a cut that contains normal butane, where said cut is isomerized before being recycled at the entry of the fractionation area of the alkylation effluents. Such an arrangement makes it possible to advantageously use the effluent fractionation area to separate the mixture of normal butane and isobutane that exits the isomerization area.

U.S. Pat. No. 4,324,937 describes a procedure for the production of gasoline type cuts from a mixture of propane and butane. This procedure includes a step for the production of isobutane through isomerization of the normal butane, a step for the production of propylene through dehydrogenation of the propane and a step for the production of superior hydrocarbons through alkylation of isobutane by propylene. The production of isobutane is guaranteed by isomerization both of the normal butane present in the starting mixture and that extracted from the effluents of the isomerization reaction. Optionally, the cut rich in n-butane can, before isomerization, be fractionated in a deisobutanizer whose function is to extract the residual isobutane from this cut, which makes it possible to move the balance of the normal butane isomerization reaction in favor of the production of isobutane.

However, so far the systems proposed in the prior art have not proven very satisfactory. In particular, despite the fact that they are potentially very advantageous, systems in which we isomerize then recycle a cut rich in n-butane extracted from the reaction effluents of the alkylation do not make it possible to reach the expected gains.

Indeed, if only one isomerization reactor is used, the yield from the conversion of normal butane to isobutane is often insufficient, and the quantity of the isobutane make-up produced by this system does not justify the investment linked to the installation and operation of the isomerization reactor.

One solution consists in using two isomerization reactors in series operating under different conditions of severity as is usually the case in the traditional normal paraffin isomerization units. However, this alternative, although it makes it possible to obtain a satisfactory yield for the isomerization of the recycling of the normal butane also doubles the investment since two reactors must be built and operated, therefore, in the end such a system not very profitable.

Continuing Applicants' research in the alkylation area, Applicants looked into these systems where a cut rich in normal butane extracted from the reaction effluents is upgraded through isomerization, and Applicants have developed a procedure that makes it possible to remedy the inconveniences of the prior art.

In particular, Applicants have discovered that, surprisingly, the fact of previously extracting from said cut rich in n-butane the compounds with 5 or more carbon atoms that are present in it, considerably increases the yield of the normal butane isomerization reaction.

Indeed, Applicants put forward the hypotheses according to which the compounds with at least five carbon atoms that are created during the alkylation reaction and are present in a more or less important quantity in the cut rich in normal butane extracted from the reaction effluents, inhibited the isomerization reaction of the normal butane by behaving as catalyst poisons. Applicants also discovered that, by rigorously controlling the content of compounds with at least 5 carbon atoms (referred to hereafter as $C_5^+$ compounds) in the cut rich in n-butane, we were able to significantly increase the efficiency and therefore the profitability of the procedure.

SUMMARY OF THE INVENTION

Applicants have thus developed a procedure for the alkylation of isobutane by olefinic hydrocarbons in which a first hydrocarbon charge rich in isobutane is put in contact with a second charge of hydrocarbons rich in light olefins, under conditions that can trigger the alkylation of the isobutane by light olefins, the effluents emitted from the reaction area are treated in a fractionation column in order to extract at least a first cut rich in alkylate, a second cut rich in normal butane, and a third cut rich in isobutane, then said third cut is recycled at the entry of the alkylation reaction area.

This procedure is characterized by the fact that said second cut rich in normal butane is purified so as to lower its content in 5 or more carbon atom compounds to a value that is less than or equal to 5% by weight, said cut purified in this manner is treated in an normal butane to isobutane isomerization reactor, it is then recycled at the entry of the alkylation effluent fractionation column.

The procedure as set forth in this invention makes it possible to beneficiate the cut rich in normal butane extracted from the alkylation reaction effluents in the best possible way, as it makes it possible to produce, from this cut, a maximum quantity of isobutane intended as feedstock for the alkylation reactor. Indeed once free from almost all the $C_5^+$ compounds it contains, this cut is subjected to an isomerization treatment, whose yield is that much higher as said cut contains less $C_5^+$ compounds. The mixture of normal butane and isobutane thus obtained is then recycled at the entry of the column used for the fractionation of the alkylation reaction effluents. For that purpose, this mixture can either be combined, upstream from the fractionation column, with the alkylation reactor effluents, or directly injected into said alkylation reaction effluents fractionation column. The mixture of normal butane and isobutane is thus fractionated in a mixture with the reaction effluents: the isobutane that was produced in the isomerization reactor is drawn from the fractionation area in a mixture with the excess isobutane emitted from the alkylation, and all of it is recycled in the alkylation unit. As to the normal butane that was not isomerized in the isomerization reactor, it is drawn off mixed with the normal butane that is present in the alkylation reaction effluents and all of it is directed toward the $C_5^+$ compounds extraction system then toward the isomerization reactor.

Therefore, one major advantage of the procedure as set forth in the invention is that it makes it possible to substantially increase the quantity of the third cut rich in isobutane drawn from the reaction effluent fractionation column in order to be recycled toward the alkylation reactor. This gives the refiner the opportunity to either increase the alkylation unit's production capacity, or, for a constant production capacity, to decrease the input of fresh isobutane in the alkylation reactor. The profitability of the unit is thus substantially increased.

Another advantage of the procedure as set forth in the invention is that is renders unnecessary the use of two isomerization reactors in series for the transformation of the normal butane extracted from the reaction effluents to isobutane. Indeed, once purified, meaning free of the $C_5^+$ compounds, said second cut rich in normal butane can be isomerized with a satisfactory yield in one single isomerization reactor. As the cost of building and operating a $C_5^+$ elimination system is much lower than the cost of a second isomerization reactor, the procedure as set forth in the invention offers an efficient solution, while limiting investments. Compared with the systems of the prior art, the procedure as set forth in the invention therefore makes it possible to produce, at a lesser cost and with optimal efficiency, a significant isobutane make-up intended to be used as feedstock for the alkylation procedure.

This invention also relates to a device that makes it possible implement the procedure described above.

Consequently, the object of the invention is an isobutane alkylation device using olefinic hydrocarbons that contains at least:

- one alkylation reaction area, whose type is known in itself;
- one fractionation column for the effluents that emanate from said reaction area, that contains at least three levels of draw off: a lower draw off level for a first cut rich in alkylate, a middle draw off level for a second cut rich in normal butane, and a level that is higher that the prior two levels, for drawing off a third cut rich in isobutane;
- a means for recycling said third cut at the entry of the alkylation reaction area.

This device is characterized by the fact that it consists, of at least one means for selective extraction of said second cut rich in normal butane from the hydrocarbons with 5 or more carbon atoms, an isomerization reactor of normal butane to isobutane, and a means for recycling the second isomerized cut towards the entry of the fractionation column of the alkylation reaction effluents, all arranged in series.

DETAILED DESCRIPTION OF THE INVENTION

Figure 1:
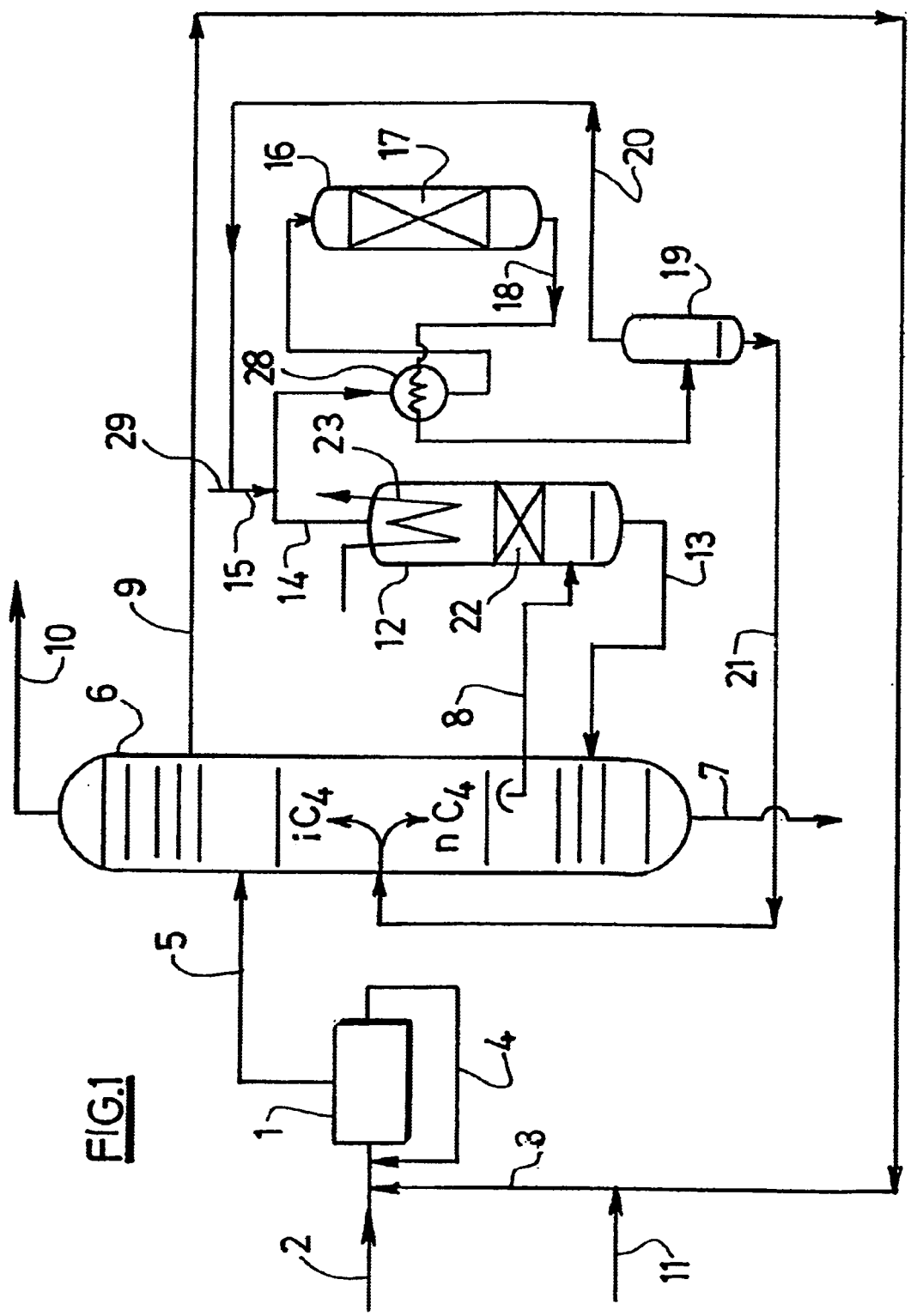
FIG. 1 is a schematic view of an alkylation unit consistent with the invention.

According to the invention, by means for selective extraction of the hydrocarbons with 5 or more carbon atoms we mean a purification system capable of selectively extracting the $C_5^+$ compounds from an oil cut, in a manner that is sufficiently developed to as to be able to reduce the content of said cut in $C_5^+$ compounds to a value that is less than or equal to 5% by weight, preferably less than or equal to 2% and, even more preferably, less than or equal to 1% by weight.

The device as set forth in the invention is proven to be fully appropriate not only when building new alkylation units but also when modernizing traditional units, in which it can be perfectly introduced without having to modify the equipment that is already in place. It only requires the addition of a $C_5^+$ elimination system, along with an isomerization reactor, and a means for recycling the second cut toward the entry of the effluent fractionation column. Therefore the device as set forth in the invention has the advantage of being particularly simple to implement, including in existing units.

According to the invention, it is essential to efficiently extract the $C_5^+$ compounds created during the alkylation reaction from said second cut rich in normal butane before directing this cut toward the isomerization reactor. Preferably, we purify this cut so as to lower its content in hydrocarbons with 5 or more carbon atoms to a value that is less than or equal to 2% by weight and, even more preferably less than or equal to 1% by weight.

The means used to this effect can be any means that make it possible to extract, in a manner that is both selective and complete, the compounds with at least 5 carbon atoms from the oil cut. Various techniques, well known to those skilled in the art, can be implemented.

Preferably, this purification step is carried out through distillation. This distillation is preferably performed with one single cut point, that can advantageously be chosen between the boiling point of the normal butane and the boiling point of the isobutane (where these two points depend of course on the pressure at which the distillation is performed). Said second cut rich in normal butane is then purified through distillation in order to obtain, on the one hand, a top cut that makes up said second purified cut and contains the normal butane and the compounds that are lighter than it is, and, on the other hand, a bottom cut that contains the $C_5^+$ compounds.

Said means for extracting the $C_5^+$ compounds then consists of a distillation column, that can for example be a plate column or a packing column. Of course, this column must contain a sufficient number of plates, or have packing that is high enough to allow the $C_5^+$ compounds to separate completely enough to lower the content to the required value.

In a particularly advantageous manner, said distillation column is a rectifying column (also called rectifier), meaning a simplified distillation column that only contains a rectifying area, but no exhausting section. This type of column has the advantage of being particularly efficient for the type of purification that is projected, while requiring only moderate investments.

Other purification techniques are available to those skilled in the art and can be used in place of or in addition to distillation, such as for example separations over molecular sieves.

The $C_5^+$ compounds that are extracted from said second cut can for example be reintroduced in the fractionation column of the alkylation reaction effluents, or combined with the alkylate that is drawn off in the bottom of this column.

The isomerization step of the normal butane present in said purified second cut is performed according to traditional methods, with the uniqueness that this step is preferably performed in one single isomerization reactor. This reactor contains an appropriate catalyst, which can be any catalyst that can handle the isomerization reaction of normal butane. Such catalysts, well known to those skilled in the art, are usually made of superacid solid particles.

In particular, we can advantageously use a sulfated zirconia base catalyst linked to a group VIII metal of the Periodic table of the elements, such as for example the catalyst described in the application for patent EP 908 232 in the name of Applicants.

In an even more advantageous manner, we use a catalyst that contains, arranged on a support such as alumina, a group VIII metal of the Period table of the elements linked to acid sites of the Lewis type sites, meaning metallic halides with the formula $—OMX_2$, where X is a halogen, in particular chlorine, and M is a metal, in particular aluminum. When they are implemented, it is preferable to activate these catalysts by transforming Lewis sites into Brönsted sites with a formula $—OMX_3H$, through halogenation using a halogenating agent such as hydrochloric acid, as described for example in the applications for patent WO 98/25699 and WO 97/19752.

The operating conditions in which the isomerization of the normal butane takes place are also known. The cut to be isomerized is combined with hydrogen according to a hydrogen-to-hydrocarbon molecular ratio preferably ranging between 0.005 and 10, then circulates, at a pressure ranging preferably between $5.10^5$ and $50.10^5$ Pa and at a temperature that preferably ranges between 100 and 300° C., in the isomerization reactor that contains one or several catalyst beds. These operating conditions are advantageously optimized so that the entire reaction mixture is in a vapor phase in the isomerization reactor.

Upon exiting the isomerization reactor, the isomerized second cut is then recycled at the entry of the fractionation column of the alkylation reaction effluents. According to one particularly advantageous method of execution it is directly reintroduced in said column, at a level that is preferably greater than the level at which the draw off of said second cut rich in normal butane is performed. In an even more preferred manner, it is reintroduced at an intermediate level between the draw off level of said second cut rich in normal butane and the draw off level of said third cut rich in isobutane.

Two hydrocarbon charges feed the procedure as set forth in the invention. The first charge is a hydrocarbon cut rich in isobutane, preferably containing at least 70% by weight of isobutane.

The second charge is a hydrocarbon cut rich in light olefins, meaning in mono-olefins that contain from 2 to 12 atoms of carbon. Preferably, said second charge contains a substantial quantity of mono-olefins that contain 3 to 5 carbon atoms: it advantageously contains at least 30% by weight of such olefins. Even more preferably, said second charge contains at least 40% by weight of butenes.

Advantageously, said second charge comes, all or in part, from effluents of a heavy oil cuts cracking unit such as in particular a catalytic cracking unit. Advantageously, such a charge can, prior to its introduction in the procedure as set forth in the invention, have been subjected to a hydrotreatment with the intent to isomerize the mono-olefins and/or selectively hydrogenate the diolefins that are present.

The invention does not relate to the conditions in which the alkylation of the isobutane using light olefins is carried out. We can indeed use any known system, and currently those skilled in the art have several alternatives at their disposal. The alkylation reaction area may include one or several reactors, in which the two charges are put in contact in the presence of a catalyst usually of acid type. This catalyst can be liquid (in particular hydrofluoric acid or sulfuric acid) or solid (such as for example the catalyst described in the application for patent WO/97.25141). The operating conditions are also known to those skilled in the art. They usually include a low temperature, preferably ranging between $-10$ and 150° C., and preferably between 0 and 100° C. The pressure is advantageously chosen at a value that is high enough to maintain the reaction mixture in liquid phase when in contact with the catalyst. The isobutane-to-olefin molar ratio advantageously ranges between 3 and 15.

Figure 2:
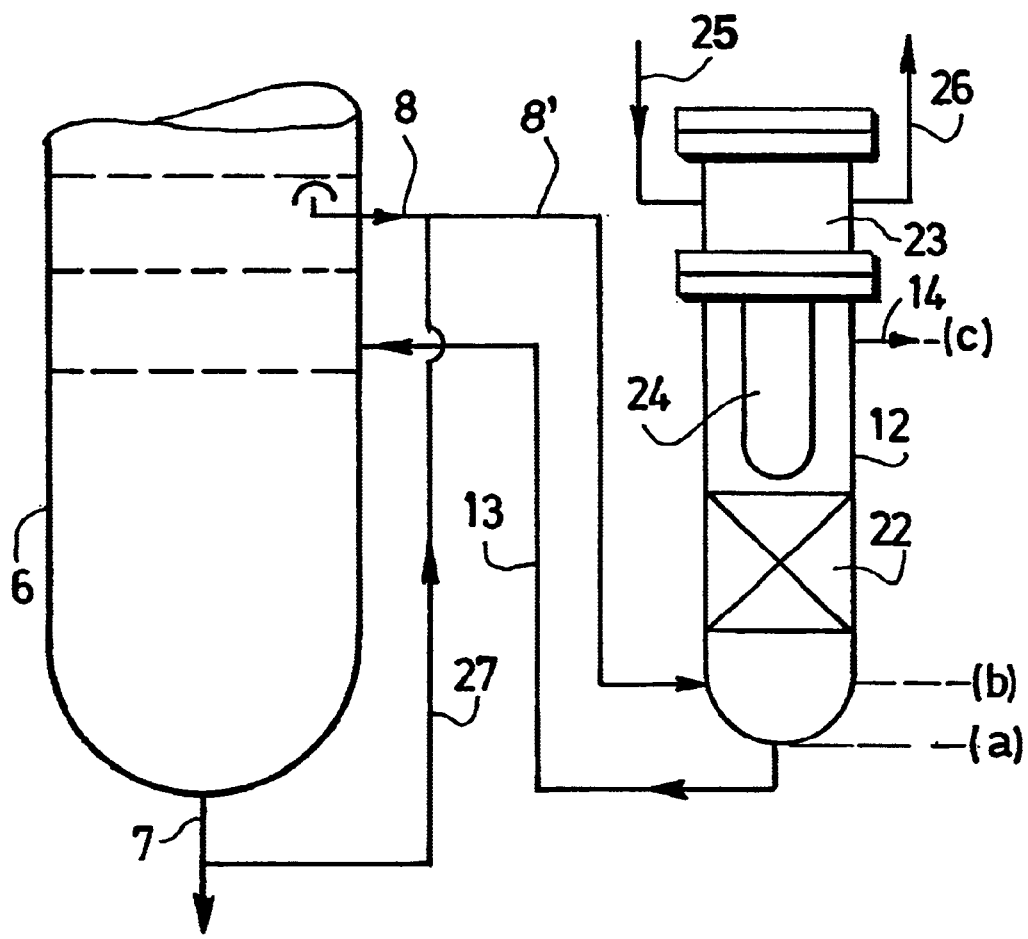
FIG. 2 is a more detailed view of a normal butane rectifier, which is a preferred means for extracting the $C_5^+$ compounds from said second cut rich in normal butane.

Other characteristics and advantages of the invention will become apparent when reading the description of the various methods of execution, given hereafter in reference to the attached drawings, where:

FIG. 1 is a schematic view of an alkylation unit consistent with the invention;

FIG. 2 is a more detailed view of an normal butane rectifier, which is a preferred means for extracting the $C_5^+$ compounds from said second cut rich in normal butane.

In reference to FIG. 1, a first hydrocarbon charge 3 rich in isobutane and a second hydrocarbon charge 2 rich in light olefins feed an alkylation reactor 1 that operates in the presence of an acid catalyst, for example liquid, such as hydrofluoric acid.

At the reactor's output, the acid is recuperated and reintroduced into the unit through line 4, and the reaction effluents are directed through line 5 toward the fractionation column 6, where they are separated through distillation so as to extract:

- a first cut rich in alkylate, drawn from the bottom of the column 6 through line 7;
- a second cut rich in normal butane, drawn from the column 6 through line 8;
- a third cut rich in isobutane, drawn from the column 6 through line 9;
- a fourth cut, drawn from the top of the column 6 through line 10 and containing the light compounds: hydrocarbons with less than four carbon atoms, residual hydrofluoric acid, hydrogen.

The third cut rich in isobutane and drawn through line 9 is recycled toward the alkylation reaction area: it meets up with line 3 that feeds the alkylation reactor 1. In parallel, line 11 makes it possible to bring a fresh isobutane make-up to the feed line 3 where it is added to the recycled isobutane.

The second cut rich in normal butane is moved along through line 8 toward the enclosure 12, in which it is purified by distillation so as to lower its content in five or more carbon atom compounds to a value that is less than or equal to 5% by weight. The flow of $C_5^+$ compounds extracted from said second cut is drawn off from the enclosure 12 through line 13, and is reinjected into the column 6 at a level that is preferably less than the draw off level of said second cut.

The purified second cut, drawn at the top of the enclosure 12, is moved along through line 14 toward the isomerization reactor 16. It is mixed with a gas that is rich in hydrogen, wherein the hydrogen-rich gas is introduced via line 15, and the hydrogen-rich gas is residual hydrogen that is moved along through line 20 and/or a fresh hydrogen make-up that is moved along through line 29. The mixture that results therefrom, after having passed through the heat exchanger 28, is introduced into the isomerization reactor 16 where it passes through an isomerization catalyst bed 17. The effluents of the reactor 16 that are evacuated through line 18 pass through the heat exchanger 28 before being introduced into the flash vessel 19, in which the residual hydrogen is recuperated and recycled upstream from the isomerization reactor 16 through line 20.

The second cut isomerized in this manner is then recycled through line 21 toward the alkylation effluent fractionation column 6, where it is advantageously injected at an intermediate level between the (lower) level of the draw off of said second cut rich in normal butane, and the (higher) level of the draw off of said third cut rich in isobutane.

FIG. 2 represents, in more detail, a preferred method of execution for the purification enclosure 12 of the second cut rich in normal butane. This enclosure consists of a distillation column and, more precisely, of a normal butane rectifier, that makes it possible to lower this cut's $C_{5+}$ compounds content to a value that is less than 1% by weight. This column has two draw-off levels: an upper draw-off level (c), through line 14, for said second rectified cut (meaning weakened in $C_{5+}$ compounds), and a lower draw-off level (a), through line 13, for a cut that contains the $C_{5+}$ compounds.

Said second cut rich in normal butane, extracted from the alkylation effluents fractionation column 6, is moved through the successive lines 8 and 8' toward the rectifier 12, where it is introduced at an intermediate level (b) between the two draw off levels (a) and (c).

Between the introduction level (b) of said second cut and the draw off level (c) of this purified cut, there is a rectifying section that consists of a packing bed 22. At the top of the rectifier 12, a condenser 23 is fed in cooling fluid, for example water, that is moved along through line 25, circulates in the exchanger 24 and is evacuated through line 26. The condensation system represented here is a condensation system that is internal to the rectifying column 12. Of course, other systems, known to those skilled in the art, can be implemented, such as condensation systems external to the column 12.

As an option, line 27 offers the possibility of combining a fraction of the alkylate, drawn from the column 6 through line 7, with said second cut rich in normal butane, drawn from the column 6 through line 8. The mixture is then moved along toward the rectifier 12 through line 8'. This makes is possible to improve the purification step of said second cut rich in normal butane, while helping pull the $C_5^+$ compounds down toward the bottom of the rectifier.

The following examples, not to be considered as limiting, are only intended to illustrate the implementation and advantages of the invention.

EXAMPLES

Comparative Example 1

Three tests were carried out in an experimental alkylation unit, consisting of a reactor in which a first charge rich in isobutane is put in contact with a second charge rich in olefins, in the presence of a liquid acid catalyst (hydrofluoric acid) at a temperature of 40° C. and at a pressure of $15.10^5$ Pa.

For these three tests, one same charge rich in light olefins is used. Its flow is of 25000 kg/h and its composition is as follows:

| Hydrocarbons | % by weight |
| --- | --- |
| Propane | Traces |
| Isobutane | 27.6 |
| Butenes | 59.8 |
| Normal butane | 12.0 |
| $C_5^+$ | 0.6 |

The first test, E1, is carried out in a unit that is consistent with that represented in FIG. 1, consisting of a normal butane rectifier 12, but no normal butane isomerization reactor 16. Consequently, after purification in the rectifier 12, the second cut rich in normal butane is extracted from the unit to be for example sold as such.

The following table illustrates the results of this test in terms of composition in kg/h of the hydrocarbon flows that circulate in various lines of the unit:

|  | Line 11 (isobutane make-up) | Line 3 (total isobutane) | Line 9 (recycled isobutane) | Line 7 (alkylate) |
|---|---|---|---|---|
| Propane | 74 | 406 | 331 | 0 |
| Isobutane | 11748 | 142482 | 130734 | 2 |
| Butenes | 0 | 0 | 0 | 0 |
| Normal butane | 597 | 16831 | 16234 | 504 |
| $C_5^+$ | 0 | 3525 | 3525 | 30506 |
| Total hydrocarbon flow | 12419 | 163244 | 150824 | 31012 |

The second test, E2, is carried out in a unit that is consistent with the one represented in FIG. 1, but does not include the normal butane rectifier 12; the second cut rich in normal butane drawn from the fractionation column 6 is introduced directly into the normal butane isomerization reactor 16. Measurements have shown that the content of this cut in $C_5^+$ compounds is of 23% by weight.

The following table illustrates the results of this test in terms of composition in kg/h of the hydrocarbon flows in the various lines:

|  | Line 11 (isobutane make-up) | Line 3 (total isobutane) | Line 9 (recycled isobutane) | Line 7 (alkylate) |
|---|---|---|---|---|
| Propane | 62 | 485 | 422 | 0 |
| Isobutane | 9838 | 142482 | 132644 | 20 |
| Butenes | 0 | 0 | 0 | 0 |
| Normal butane | 500 | 21973 | 21473 | 1394 |
| $C_5^+$ | 0 | 3637 | 3637 | 30530 |
| Total hydrocarbon flow | 10400 | 168577 | 158176 | 31944 |

The third test, E3, is carried out as set forth in the invention, in a unit that is consistent with the unit represented in FIG. 1. In particular, said second cut rich in normal butane drawn through line 8 is purified in the rectifier 12, so as to lower the content in $C_5^+$ compounds to a value of 0.5% by weight. The cut that is purified in this way is then treated in the normal butane isomerization reactor 16, then recycled at the entry of the fractionation column 6 of the alkylation reaction effluents.

The following table illustrates the results of this test in terms of composition in kg/h of the hydrocarbon flows in the various lines:

|  | Line 11 (isobutane make-up) | Line 3 (total isobutane) | Line 9 (recycled isobutane) | Line 7 (alkylate) |
|---|---|---|---|---|
| Propane | P | 504 | 446 | 0 |
| Isobutane | 9193 | 142482 | 133289 | 2 |
| Butenes | 0 | 0 | 0 | 0 |
| Normal butane | 467 | 22987 | 22521 | 699 |
| $C_5^+$ | 0 | 3529 | 3529 | 30532 |
| Total hydrocarbon flow | 9718 | 169502 | 159785 | 31233 |

The three tests above were carried out with a constant total flow of isobutane (142482 kg/h) introduced through line 3 into the alkylation reactor. The alkylate yield ($C_5^+$ flow drawn through line 7) remains roughly constant (in the 30530 kg/h range). In other words, the quantity of isobutane recycled through line 9 was completed by adjusting the flow of make-up isobutane that was moved through line 11.

Comparison of the results of tests E1 and E2 makes it possible to see the beneficial effect of the introduction of a reactor 16 that performs the isomerization of the normal butane to isobutane that is recycled at the entry of the fractionation column 6. Indeed, this makes it possible to substantially reduce the fresh isobutane make-up introduced into the unit through line 11: from 11748 kg/h in test E1, it drops to 9838 kg/h in test E2, or a reduction of 16.25%.

Test E3 shows the additional improvement tied to the implementation of the procedure in accordance with the invention. Indeed this time the fresh isobutane make-up introduced into the unit through line 11 is of 9193 kg/h, or a gain of 21.75% compared with test E1, and a gain of 6.55% compared with test E2. Thus, the invention makes possible an optimal beneficiation of the second cut rich in normal butane extracted from the reaction effluents: an appropriate purification of this cut followed by an isomerization of the normal butane makes it possible to produce a maximum quantity of isobutane intended to refeed the alkylation reactor. The profitability of the unit is significantly improved because, for a same alkylate yield, the consumption of fresh isobutane, produced in a relatively costly manner, is markedly reduced.

Comparative example 2

This example, performed under the conditions as test E3 above, illustrates the influence of the degree of purification, in the rectifier 12, of said second cut rich in normal butane.

Three tests E4, E5 and E6 were carried out where the operating conditions of the normal butane rectifier were changed, so as to change the content in $C_5^+$ compounds of said second cut introduced through line 14 into the isomerization reactor 16.

For the three tests, the operating conditions of the isomerization reactor are identical:

temperature: 155° C.

pressure: $30.10^5$ Pa, hydrogen-to-hydrocarbon molecular ratio: 0.5 pph (weight of charge per catalyst unit weight and per hour): 1 $h^{-1}$ catalyst: aluminum chloride and platinum base deposited on an alumina support.

The following table illustrates the results obtained in terms of yield of the isomerization reaction of the normal butane to isobutane carried out in the reactor (16), based on the composition of the flow introduced in line (14) into this reactor.

| Test | Content of $C_4$ Compounds (% by weight) | Content of $C_5^+$ compounds (% by weight) | Yield of the reaction normal butane → isobutane |
|---|---|---|---|
| E3 | 91 | 9 | 59% |
| E4 | 99.4 | 0.6 | 61% |
| E5 | 99.99 | 0.01 | 61.8% |

This test illustrates the beneficial effect of a thorough extraction of the $C_5^+$ compounds from the second cut rich in normal butane prior to the isomerization of the latter. For tests E4 and E5, carried out in accordance with the invention, we obtain a better yield of the isomerization reaction of the normal butane, compared with test E3 where too large a quantity of $C_5^+$ tends to inhibit the reaction. Thus, the fact of sufficiently reducing the content of said second cut in $C_5^+$ compounds makes it possible to produce more recycling isobutane, and therefore improve the performances and the profitability of the alkylation unit.

What is claimed is:

1. A process for the alkylation of isobutane by olefinic hydrocarbons, comprising the steps of:

contacting a first hydrocarbon charge rich in isobutane (3) with a second hydrocarbon charge rich in light olefins (2), under conditions that will provoke the alkylation of the isobutane by light olefins;

treating the effluents that emanate from a reaction area in a fractionation column (6) in order to extract at least a first cut rich in alkylate (7), a second cut rich in normal butane (8), and a third cut rich in isobutane (9); and recycling said third cut rich in isobutane (9) at an entry of an alkylation reaction area;

wherein said second cut rich in normal butane (8) has a content of compounds with 5 or more carbon atoms that is more than 0.5 wt %, and said second cut rich in normal butane (8) is purified (12) by distillation with one single cut point chosen between the boiling point of normal butane and the boiling point of iso-pentane so as to lower its content in compounds with 5 or more carbon atoms to a value that is less than or equal to 0.5 wt %, and wherein said second cut thus purified (14) is treated in an isomerization reactor (16) of the normal butane to isobutane, and said second cut thus purified and treated (21) is recycled at an entry of an alkylation effluent fractionation column (6).

2. The process as set forth in claim 1, wherein the isomerization of the normal butane present in said second cut thus purified (14) is carried out in one single isomerization reactor (16).

3. The process as set forth in claim 1, wherein said second cut thus purified and treated (21) is directly reintroduced into the alkylation effluent fractionation column (6).

4. The process as set forth in claim 1, wherein said second cut thus purified and treated (21) is injected in the alkylation effluent fractionation column (6) at a level higher than a level at which draw off of said second cut rich in normal butane (8) is carried out.

5. The process as set forth in claim 4, wherein said second cut thus purified and treated (21) is injected in the alkylation effluent fractionation column (6) at an intermediate level between the draw off level of said second cut rich in normal butane (8) and the draw off level of said third cut rich in isobutane (9).

6. The process as set forth in claim 1, wherein, between the alkylation effluent fractionation column (6) and the distillation column (12), a fraction of alkylate (27) is combined with said second cut rich in normal butane (8) to form a mixture (8'), and said mixture is then purified through distillation (12).

7. The process as set forth in claim 1, wherein a catalyst present in the isomerization reactor (16) is a sulphated zirconia base catalyst linked to a group VIII metal from the Periodic table of the elements.

8. The process as set forth in claim 1, wherein a catalyst present in the isomerization reactor (16) is a catalyst that contains, deposited on a support, a group VIII metal of the Periodic table of the elements linked to Lewis acid sites that were transformed, upon implementation, into Brönsted sites, having a formula —$OMX_3H$, through halogenation by a halogenating agent.

9. The process as set forth in claim 8, wherein the support is alumina.

10. The process as set forth in claim 8, wherein the Lewis acid sites are metallic halides having a formula —$OMX_2$, where X is a halogen and M is a metal.

11. The process as set forth in claim 10, where the halogen X is chloride and the metal M is aluminum.

12. The process as set forth in claim 8, wherein the halogenating agent is hydrochloric acid.

13. The process as set forth in claim 1, further comprising the steps of:

combining said second cut thus purified (14) with hydrogen according to a hydrogen-to-hydrocarbon molecular ratio ranging between 0.005 and 10; and treating in an isomerization reactor (16) containing at least one catalyst bed said second cut thus purified (14) combined with hydrogen by circulating said second cut thus purified (14) combined with hydrogen at a pressure ranging between $5.10^5$ and $50.10^5$ Pa and at a temperature ranging between 100 and 300° C.

* * * * *